US012370210B2

United States Patent
Gomperts

(10) Patent No.: US 12,370,210 B2
(45) Date of Patent: Jul. 29, 2025

(54) CARBON MONOXIDE AS A TREATMENT FOR NEURODEGENERATIVE DISEASE

(71) Applicant: The General Hospital Corporation, Boston, MA (US)

(72) Inventor: Stephen Gomperts, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 674 days.

(21) Appl. No.: 17/616,110

(22) PCT Filed: Jun. 5, 2020

(86) PCT No.: PCT/US2020/036433
§ 371 (c)(1),
(2) Date: Dec. 2, 2021

(87) PCT Pub. No.: WO2020/247825
PCT Pub. Date: Dec. 10, 2020

(65) Prior Publication Data
US 2022/0296636 A1   Sep. 22, 2022

Related U.S. Application Data

(60) Provisional application No. 62/858,015, filed on Jun. 6, 2019.

(51) Int. Cl.
| *A61K 33/00* | (2006.01) |
| *A61K 9/00* | (2006.01) |
| *A61K 9/08* | (2006.01) |
| *A61P 25/16* | (2006.01) |
| *A61P 25/28* | (2006.01) |

(52) U.S. Cl.
CPC ............ *A61K 33/00* (2013.01); *A61K 9/0053* (2013.01); *A61K 9/08* (2013.01); *A61P 25/16* (2018.01); *A61P 25/28* (2018.01)

(58) Field of Classification Search
CPC ........ A61K 33/00; A61K 9/0053; A61K 9/08; A61P 25/28; A61P 25/16
See application file for complete search history.

(56) References Cited

U.S. PATENT DOCUMENTS

| 9,980,981 | B2 | 5/2018 | Gomperts et al. |
| 2002/0155166 | A1 | 10/2002 | Choi et al. |
| 2013/0309279 | A1 | 11/2013 | Gomperts et al. |
| 2018/0194784 | A1 | 7/2018 | Dingra et al. |

FOREIGN PATENT DOCUMENTS

WO    WO 2003094932    * 11/2003    ............. A61K 33/00

OTHER PUBLICATIONS

Belcher et al. (Plos One 13(10): e0205194 (2018)).*
American Parkinson Disease Association (2018) (APDA).*
Mahan (Medical Gas Research, 2(32) 2012 ahan (Medical Gas Research, 2(32) 2012.*
Agency for Toxic Substances and Disease Registry, "Toxological Profile for Carbon Monoxide," U.S. Department of Health and Human Services: Toxic Substances Portal, Jun. 2012, 347 pages.
Aguiar et al., "Moderate-Intensity Physical Exercise Protects Against Experimental 6-Hydroxydopamine-Induced Hemiparkinsonism Through Nrf2-Antioxidant Response Element Pathway," Neurochem Res, 2016, 41(1-2):64-72, 9 pages.
Alcaraz et al., "Anti-inflammatory actions of the heme oxygenase-1 pathway," Curr Pharm Des, 2003, 9(30):2541-2551.
Alfieri et al., "Targeting the Nrf2-Keap1 antioxidant defence pathway for neurovascular protection in stroke," J Physiol, 2011, 589(Pt 17):4125-4136.
Almeida et al., "Carbon monoxide modulates apoptosis by reinforcing oxidative metabolism in astrocytes: role of Bcl-2," The Journal of Biol Chem, Mar. 2012, 287(14):10761-70.
Bathoorn et al., "Anti-inflammatory effects of inhaled carbon monoxide in patients with COPD: a pilot study," European Respiratory J, 2007, 30:1131-7.
Becker et al., "Presentation LBP27: Oral CO as a Treatment for Stroke," Abstract, Presented at Proceedings of the Inter Stroke Conference, Houston, TX, Mar. 2017, 1 page.
Belcher et al., "MP4CO, a pegylated hemoglobin saturated with carbon monoxide, is a modulator of HO-1, inflammation and vaso-occlusion in transgenic sickle cell mice," Blood, 2013, 122:2757-2764.
Belcher et al., "Oral carbon monoxide therapy in murine sickle cell disease: beneficial effects on vaso-occlusion, inflammation and anemia," PLoS One, Oct. 2018, 13(10):e0205194, 11 pages.
Blandini et al., "Animal models of Parkinson's disease," FEBS J, Apr. 2012, 279(7):1156-66.
Blesa et al., "Classic and new animal models of Parkinson's disease," J. Biomed. Biotechnol., 2012, 2012:845618, 10 pages.
Cai et al., "Bimolecular Fluorescence Complementation of Alpha-synuclein Demonstrates its Oligomerization with Dopaminergic Phenotype in Mice," EBioMedicine, Mar. 2018, 29:13-22.
Chang et al., "Association between ischemic stroke and iron-deficiency anemia: a population-based study," PLoS ONE, Dec. 2013, 9(8):e103078, 6 pages.
Chang et al., "Increased Risk of Dementia in Patients Exposed to Nitrogen Dioxide and Carbon Monoxide: A Population-Based Retrospective Cohort Study," PLoS One, Aug. 2014, 9(8):e103078, 8 pages.
Chen et al., "The sirtuin-2 inhibitor AK7 is neuroprotective in models of Parkinson's disease but not amyotrophic lateral sclerosis and cerebral ischemia," PLoS One, Jan. 2015, 10(1):e0116919, 15 pages.
Chi et al., "CO Induces Nrf2-Dependent Heme Oxygenase-1 Transcription by Cooperating with Sp1 and c-Jun in Rat Brain Astrocytes," Mol Neurobiol., Aug. 2014, 52(1):277-92, 16 pages.

(Continued)

*Primary Examiner* — Shirley V Gembeh
(74) *Attorney, Agent, or Firm* — Fish & Richardson P.C.

(57) ABSTRACT

Methods for treating neurodegenerative diseases, e.g., Parkinson's disease (PD), with carbon monoxide (CO), e.g., orally administered CO.

8 Claims, 10 Drawing Sheets

(56) References Cited

OTHER PUBLICATIONS

Choi et al., "Dual effects of carbon monoxide on pericytes and neurogenesis in traumatic brain injury," Nat Med., Nov. 2016, 22(11):1335-1341.
Choi, "Parkinsonism after carbon monoxide poisoning," Eur Neurol., 2002, 48(1):30-3.
Chora et al., "Heme oxygenase-1 and carbon monoxide suppress autoimmune neuroinflammation," The Journal of Clinical Investigation, 2007, 117(2):438-47.
Chung et al., "Carbon monoxide, a reaction product of heme oxygenase-1, suppresses the expression of C-reactive protein by endoplasmic reticulum stress through modulation of the unfolded protein response," Mol Immunol, Sep. 2011, 48(15-16):1793-1799.
Dallas et al., "Carbon monoxide protects against oxidant-induced apoptosis via inhibition of Kv2. 1," The FASEB Journal, Jan. 2011, 25(5):1519-1530.
Dwyer et al., "Differential expression of heme oxygenase-1 in cultured cortical neurons and astrocytes determined by the aid of a new heme oxygenase antibody. Response to oxidative stress," Brain Res Mol Brain Res, May 1995, 30(1):37-47.
Fagone et al., "Therapeutic potential of carbon monoxide in multiple sclerosis," Clinical and Experimental Immunology, 2012, 167(2):179-87.
Gupta et al., "Neurotherapeutic effects of novel HO-1 inhibitors in vitro and in a transgenic mouse model of Alzheimer's disease," J Neurochem, Dec. 2014, 131(6):778-90.
Hald et al., "Oxidative stress and inflammation in Parkinson's disease: is there a causal link?," J Exp Neurol, Jun. 2005, 193(2):279-90.
Hamilton, "Lewy bodies in Alzheimer's disease: A neuropathological review of 145 cases using alpha-synuclein immunohistochemistry," Brain Pathol, Jul. 2000, 10(3):378-384.
Harms et al., "MHCII is required for a-synuclein-induced activation of microglia, CD4 T cell proliferation, and dopaminergic neurodegeneration," J Neurosci., Jun. 2013, 33(23):9592-600.
Hebert et al., "Alzheimer disease in the United States (2010-2050) estimated using the 2010 census," Neurology, May 2013, 80(19):1778-83.
Hernán et al., "A meta-analysis of coffee drinking, cigarette smoking, and the risk of Parkinson's disease," Ann Neurol, Sep. 2002, 52(3):276-84.
Hettiarachchi et al., "Heme oxygenase-1 protects against Alzheimer's amyloid-beta(1-42)-induced toxicity via carbon monoxide production," Cell Death Dis., Dec. 2014, 5(12):e1569, 11 pages.
Hirsch et al., "Neuroinflammation in Parkinson's disease," Parkinsonism Relat. Disord., 2012, 18(Suppl 1):S210-2.
Hirsch et al., "Neuroinflammation in Parkinson's disease: a target for neuroprotection?," The Lancet Neurology, 2009, 8(4):382-397.
Howard et al., "Safety and Tolerability of MP4CO: A Dose Escalation Study in Stable Patients With Sickle Cell Disease," Amer Soc Hematol, 2013, 122(21):2205, 3 pages.
Huang and Mucke, "Alzheimer mechanisms and therapeutic strategies," Cell, Mar. 2012, 148(6):1204-22.
Hung et al., "Overexpression of heme oxygenase-1 protects dopaminergic neurons against 1-methyl-4-phenylpyridinium-induced neurotoxicity," Mol Pharmacol, Oct. 2008, 74(6):1564-75.
Hunot et al., "Neuroinflammatory processes in Parkinson's disease," Ann. Neurol., 2003, 53(Suppl. 3):S49-S58.
Hurd et al., "Monetary costs of dementia in the United States," NEJM, 2013, 368(14):1326-34.
Imuta et al., "Hypoxia-mediated induction of heme oxygenase type I and carbon monoxide release from astrocytes protects nearby cerebral neurons from hypoxia-mediated apoptosis," Antioxid Redox Signal., May 2007, 9(5):543-52.
International Preliminary Report on Patentability in International Appln. No. PCT/US2020/036433, dated Dec. 16, 2021, 9 pages.
International Search Report and Written Opinion in International Appln. No. PCT/US2020/036433, dated Sep. 9, 2020, 11 pages.

Jackson-Lewis and Przedborski, "Protocol for the MPTP mouse model of Parkinson's disease," Nat Protoc., 2007, 2(1):141-51.
Jankowsky et al., "Co-expression of multiple transgenes in mouse CNS: a comparison of strategies," Biomol Eng., Jun. 2001, 17(6):157-65.
Jankowsky et al., "Mutant presenilins specifically elevate the levels of the 42 residue beta-amyloid peptide in vivo: evidence for augmentation of a 42-specific gamma secretase," Hum Mol Genet., Jan. 2004, 13(2):159-70.
Klaus et al., "Early treatment of transient focal cerebral ischemia with bovine PEGylated carboxy hemoglobin transfusion," Artificial cells, blood substitutes, and immobilization biotechnology, Oct. 2010, 38(5):223-9.
Koprich et al., "Expression of human A53T alpha-synuclein in the rat substantia nigra using a novel AAV 1/2 vector produces a rapidly evolving pathology with protein aggregation, dystrophic neurite architecture and nigrostriatal degeneration with potential to model the pathology of Parkinson's disease," Molecular Degeneration, Oct. 2010, 5:43, 13 pages.
Kumar and Bandyopadhyay, "Free heme toxicity and its detoxification systems in human," Toxicol Lett, Jul. 2005, 157(3):175-188.
Lai et al., "Increased risk of Parkinson disease in patients with carbon monoxide intoxication: a population-based cohort study," Medicine, May 2015, 94(19):e869, 6 pages.
Lai et al., "Patients With Carbon Monoxide Poisoning and Subsequent Dementia: A Population-Based Cohort Study," Medicine (Baltimore), Jan. 2016, 95(1):e2418, 7 pages.
Lee and Chau, "Heme oxygenase-1 mediates the anti-inflammatory effect of interleukin-10 in mice," Nat Med., 2002, 8(3):240-6.
Lee Mosley et al., "Neuroinflammation, oxidative stress, and the pathogenesis of Parkinson's disease," Clinical Neuroscience Research, Dec. 2006, 6(5):261-281, 34 pages.
Lin and Beal, "Mitochondrial dysfunction and oxidative stress in neurodegenerative diseases," Nature, 2006, 443(7113):787-95.
Mahan et al., "Inhaled carbon monoxide provides cerebral cytoprotection in pigs," PLoS One, 2012, 7(8):e41982, 13 pages.
Matz et al., "Heme-oxygenase-1 induction in glia throughout rat brain following experimental subarachnoid hemorrhage," Brain Res., 1996, 713(1-2):211-222.
Mayr et al., "Effects of carbon monoxide inhalation during experimental endotoxemia in humans," Am J Physiol Heart Circ Physiol, 2005, 171:354-60.
McFarland et al., "Alpha-synuclein S129 phosphorylation mutants do not alter nigrostriatal toxicity in a rat model of Parkinson disease," J Neuropathol Exp Neurol., May 2009, 68(5):515-24.
McFarland et al., "Chronic treatment with novel small molecule Hsp90 inhibitors rescues striatal dopamine levels but not α-synuclein-induced neuronal cell loss," PLoS One, Jan. 2014, 9(1):e86048, 8 pages.
Mellick et al., "Passive smoking and Parkinson disease," Neurol., 2006, 67:179-80.
Misra et al., "A Phase Ib open label, randomized, safety study of SANGUINATE™ in patients with sickle cell anemia," Rev Bras Hematol Hemoter, 2017, 39(1):20-27.
Misra et al., "PEGylated carboxyhemoglobin bovine (SANGUINATE): results of a phase I clinical trial," Artif Organs, 2014, 38(8):702-7.
Moon et al., "Carbon Monoxide Ameliorates 6-Hydroxydopamine-Induced Cell Death in C6 Glioma Cells," Biomolecules & Therapeutics, Mar. 2018, 26(2):175-181.
Morita et al., "Carbon monoxide controls the proliferation of hypoxic vascular smooth muscle cells," J Biol Chem, Dec. 1997, 272(52):32804-9.
Morita et al., "Smooth muscle cell-derived carbon monoxide is a regulator of vascular cGMP," PNAS USA, Feb. 1995, 92(5):1475-9.
Moskowitz and Lo, "Neurogenesis and apoptotic cell death," Stroke, 2003, 34(2):324-326.
Motterlini and Otterbein, "The therapeutic potential of carbon monoxide," Nat Rev Drug Discov., Sep. 2010, 9(9): 728-43, 18 pages.
Motterlini et al., "Carbon monoxide-releasing molecules: characterization of biochemical and vascular activities," Circ Res, 2002, 90(2):E17-E24, 15 pages.

(56) References Cited

OTHER PUBLICATIONS

Munoz et al., "Targeting p38 MAPK pathway for the treatment of Alzheimer's disease," Neuropharmacology, Mar. 2010, 58(3):561-8.
Murray et al., "Neuropathologically defined subtypes of Alzheimer's disease with distinct clinical characteristics: A retrospective study," Lancet Neurol, Sep. 2011, 10(9):785-796.
Musiek and Holtzman, "Three dimensions of the amyloid hypothesis: time, space and 'wingmen'," Nat Neurosci., Jun. 2015, 18(6):800-6.
Nagatsu et al., "Cytokines in Parkinson's disease," J Neural Trans Suppl, 2000, 58:143-51.
Naoi and Maruyama, "Cell death of dopamine neurons in aging and Parkinson's disease," Mech Aging Dev., Nov. 1999, 111(203):175-188.
Natanson et al., "Cell-free hemoglobin-based blood substitutes and risk of myocardial infarction and death: a meta-analysis," JAMA, May 2008, 299(19):2304-12.
Nunomura et al., "Oxidative damage is the earliest event in Alzheimer disease," Journal of Neuropathology and Experimental Neurology, 2001, 60(8):759-767.
Olanow, "Oxidation reactions in Parkinson's disease," Neurology, 1990, 40(10 Suppl 3):32-37.
Opii et al., "Proteomic identification of brain proteins in the canine model of human aging following a long-term treatment with antioxidants and a program of behavioral enrichment: relevance to Alzheimer's disease," Neurobiol Aging, Jan. 2008, 29(1):51-70.
Otterbein et al., Carbon monoxide has anti-inflammatory effects involving the mitogen-activated protein kinase pathway. Nat Med. 2000; 6:422-8.
Otterbein et al., "Heme oxygenase-1: unleashing the protective properties of heme," Trends in Immunol, 2003, 24(8):449-55.
Pae et al., "Carbon monoxide produced by heme oxygenase-1 suppresses T cell proliferation via inhibition of IL-2 production," J Immunol, 2004, 172:4744-51.
Parkkinen et al., "Regional distribution of alpha-synuclein pathology in unimpaired aging and Alzheimer disease," J Neuropathol Exp Neurol, Apr. 2003, 62(4):363-367.
PDF.org [online], "Statistics on Parkinson's," available on or before Apr. 4, 2017, via Internet Archive: Wayback Machine URL<http://web.archive.org/web/20170404003855/www.pdf.org/en/parkinson_statistics>, retrieved on Nov. 29, 2022, URL<www.pdf.org/en/parkinson_statistics>, 2 pages.
Pearce and Jones, "Smoking and anesthesia: preoperative abstinence and perioperative morbidity," Anes, Nov. 1984, 61(5):576-84.
Phani et al., "Neurodegeneration and Inflammation in Parkinson's disease," Park Relat Disord, Jan. 2012, 18(Suppl 1):S207-9.
Popescu et al., "Lewy bodies in the amygdala: Increase of alpha-synuclein aggregates in neurodegenerative diseases with tau-based inclusions," Arch Neurol, 2004, 61:1915-1919.
Prabhakar et al., "Carbon monoxide: A role in carotid body chemoreception," PNAS, 1995, 92(6):1994-1997.
Queiroga et al., "Carbon monoxide and the CNS: challenges and achievements," Br J Pharmacol., 2015, 172(6): 1533-45.
Queiroga et al., "Paracrine effect of carbon monoxide—astrocytes promote neuroprotection through purinergic signaling in mice," J Cell Sci, Aug. 2016, 129(16):3178-88.
Ransohoff, "How neuroinflammation contributes to neurodegeneration," Science, Aug. 2016, 353(6301):777-83.
Report.NIH.gov [online], "Parkinson's Disease Fact Sheet," available on or before Apr. 28, 2017, via Internet Archive: Wayback Machine URL <http://web.archive.org/web/20170428034809/report.nih.gov/NIHfactsheets/ViewFactSheet.aspx?csid=109>, URL</report.nih.gov/NIHfactsheets/ViewFactSheet.aspx?csid=109>, 2 pages.
Rhodes et al., "Carbon monoxide, skeletal muscle oxidative stress, and mitochondrial biogenesis in humans," Am J Physiol Heart Circ Physiol, 2009, 297:H392-9.
Ritz et al., "Pooled analysis of tobacco use and risk of Parkinson disease," Arch Neurol., Jul. 2007, 64(7):990-7.
Sato et al., "Authentically Phosphorylated α-Synuclein at Ser129 Accelerates Neurodegeneration in a Rat Model of Familial Parkinson's Disease," Neurobiol. Dis., Nov. 2011, 31(46):16884-16894.
Sawle et al., "Carbon monoxide-releasing molecules (CO-RMs) attenuate the inflammatory response elicited by lipopolysaccharide in RAW264. 7 murine macrophages," Br J Pharmacol., Jul. 2005, 145(6):800-810.
Schallner et al., Microglia regulate blood clearance in subarachnoid hemorrhage by heme oxygenase-1. The Journal of Clinical Investigation 2015; 125:2609-25.
Schipper and Song, "A heme oxygenase-1 transducer model of degenerative and developmental brain disorders," Int J Mol Sci, Mar. 2015, 16(3):5400-19.
Schipper et al., "Expression of heme oxygenase-1 in the senescent and Alzheimer-diseased brain," Ann Neurol., Jun. 1995, 37(6):758-68.
Schipper et al., "Neural Heme Oxygenase-1 Expression in Idiopathic Parkinson's Disease," Exp Neurol, Mar. 1998, 150(1):60-68.
Scott et al., "Family-based case-control study of cigarette smoking and Parkinson disease," Neurol, Feb. 2005, 64(3):442-7.
Shin et al., "Pretreatment with CO-releasing molecules suppresses hepcidin expression during inflammation and endoplasmic reticulum stress through inhibition of the STAT3 and CREBH pathways," Blood, Mar. 2012, 119(11):2523-2532.
Smith et al., "Heme oxygenase-1 is associated with the neurofibrillary pathology of Alzheimer's disease," Am J Pathol, Jul. 1994, 145(1):42-7.
Smith et al., "Oxidative stress in Alzheimer's disease," Biochim Biophys Acta., Jul. 2000, 1502(1):139-44.
Stewart et al., "Experimental human exposure to carbon monoxide," Arch Environ Health, Aug. 1970, 21(2):154-164.
Stewart, "The effect of carbon monoxide on humans," Annu Rev Pharmacol., 1975, 15:409-23.
Suliman and Piantadosi, "Mitochondrial biogenesis: regulation by endogenous gases during inflammation and organ stress," Curr Pharm Des, 2014, 20(35):5653-62, 22 pages.
Sultana and Butterfield, "Role of oxidative stress in the progression of Alzheimer's disease," Journal of Alzheimer's disease: JAD, 2010, 19(2010):341-353.
Sutherland et al., "Cerebral heme oxygenase 1 and 2 spatial distribution is modulated following injury from hypoxia-ischemia middle cerebral artery occlusion in rats," Neurosci Res., 2009, 65(4):326-334.
Tanner et al., "Smoking and Parkinson's disease in twins," Neurol, Feb. 2002, 58(4):581-8.
Theodore et al., "Targeted Overexpression of Human a-Synuclein Triggers Microglial Activation and an Adaptive Immune Response in a Mouse Model of Parkinson Disease," J Neuropathol Exp Neurol., Dec. 2008, 67(12):1149-58.
Thomas et al., "Impaired Complex-I Mitochondrial Biogenesis in Parkinson Disease Frontal Cortex," J Parkinsons Dis, 2012, 2(1):67-76.
Tsai et al., "CO-releasing molecules CORM2 attenuates angiotensin II-induced human aortic smooth muscle cell migration through inhibition of ROS/IL-6 generation and matrix metalloproteinases-9 expression," Redox Biol, Mar. 2017, 12:377-388, 14 pages.
Uchikado et al., "Alzheimer disease with amygdala Lewy bodies: A distinct form of alpha-synucleinopathy," J Neuropathol Exp Neurol, Jul. 2006, 65(7):685-697.
United States Environmental Protection Agency, "Quantitative Risk and Exposure Assessment for Carbon Monoxide—Amended Standards," Jul. 2010, 376 pages.
Valente et al., "Hereditary early-onset Parkinson's disease caused by mutations in PINK1," Science, May 2004, 304(5674):1158-1160.
Vieira et al., "Preconditioning induced by carbon monoxide provides neuronal protection against apoptosis," J Neurochem, Oct. 2008, 107(2):375-384.
Wang et al., "Carbon Monoxide Improves Neurologic Outcomes by Mitochondrial Biogenesis after Global Cerebral Ischemia Induced by Cardiac Arrest in Rats," Int J Biol Sci, Jul. 2016, 12(8):1000-9.

(56) References Cited

OTHER PUBLICATIONS

Wang et al., "Carbon monoxide-activated Nrf2 pathway leads to protection against permanent focal cerebral ischemia," Stroke, Sep. 2011, 42(9):2605-10, 12 pages.

Wang et al., "Inhibition of beta-amyloid-induced neurotoxicity by pinocembrin through Nrf2/HO-1 pathway in SH-SY5Y cells," J Neurol Sci., Sep. 2016, 368:223-30.

Winburn et al., "Cell damage following carbon monoxide releasing molecule exposure: implications for therapeutic applications," Basic & clinical pharmacology & toxicology, Jul. 2012, 111(1):31-41.

Wirdefeldt et al., "Risk and protective factors for Parkinson's disease: a study in Swedish twins," Ann Neurol., Jan. 2005, 57(1):27-33.

Yabluchanskiy et al., "CORM-3, a carbon monoxide-releasing molecule, alters the inflammatory response and reduces brain damage in a rat model of hemorrhagic stroke," Critical care medicine, 2012, 40(2):544-52, 10 pages.

Yamamoto et al., "Elevation of heme oxygenase-1 by proteasome inhibition affords dopaminergic neuroprotection," J Neurosci Res, Feb. 2010, 88(9):1934-42.

Youn et al., "PEP-1-HO-1 prevents MPTP-induced degeneration of dopaminergic neurons in a Parkinson's disease mouse model," BMB Rep, Oct. 2014, 47(10):569-74.

Zeynalov and Dore, "Low Doses of Carbon Monoxide Protect Against Experimental Focal Brain Ischemia," Neurotoxicity Research, Feb. 2009, 15(2):133-137.

Zhang et al., "4Aβ1-15-Derived Monoclonal Antibody Reduces More Abeta Burdens and Neuroinflammation than Homologous Vaccine in APP/PS1 Mice," Curr Alzheimer Res., 2015, 12(4):384-97.

Zhang et al., "Carbon monoxide differentially modulates STAT1 and STAT3 and inhibits apoptosis via a phosphatidylinositol 3-kinase/Akt and p38 kinase-dependent STAT3 pathway during anoxia-reoxygenation injury," J Biol Chem., Mar. 2005, 280(10):8714-8721.

Zhang et al., "Transfusion of hemoglobin-based oxygen carriers in the carboxy state is beneficial during transient focal cerebral ischemia," Journal of Applied Physiology, Dec. 2012, 113(11):1709-17.

Zimmerman et al., "Cerebroprotective effects of the CO-releasing molecule CORM-A1 against seizure-induced neonatal vascular injury," Amer J Phys Heart & Circ Phys, Oct. 2007, 293(4):H2501-7.

\* cited by examiner

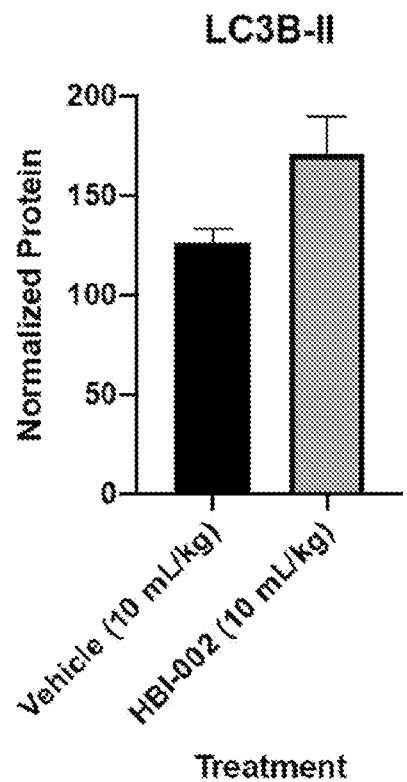
FIG. 6C
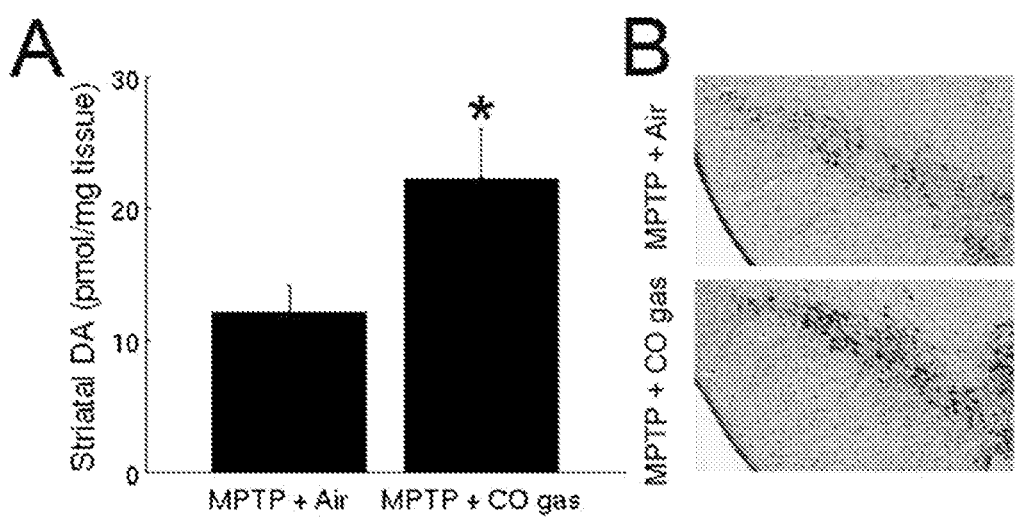
FIGs. 7A-B

CARBON MONOXIDE AS A TREATMENT FOR NEURODEGENERATIVE DISEASE

CLAIM OF PRIORITY

This application is a § 371 National Stage Application of PCT/US2020/036433, filed Jun. 5, 2020, which claims the benefit of U.S. Provisional Application Ser. No. 62/858,015, filed on Jun. 6, 2019. The entire contents of the foregoing are incorporated herein by reference.

TECHNICAL FIELD

Described herein are methods for treating neurodegenerative diseases, e.g., Parkinson's disease (PD), with carbon monoxide (CO), e.g., orally administered CO.

BACKGROUND

No treatments exist to reverse, arrest, or slow the course of neurodegenerative diseases including Alzheimer's disease (AD) and Parkinson's disease (PD), the most common neurodegenerative diseases worldwide and leading causes of death and long-term disability. Current treatment strategies for these progressive and fatal diseases are symptomatic and do not slow the disease course. Thus, there is a significant need to identify neuroprotective therapies that can impact the course of PD and AD, and prolong survival of neurons and other brain cells.

SUMMARY

In both the genetic AAV-αsynuclein A53T (AAV-aSyn) rat model and the toxin MPTP (MPTP) mouse model of PD, the present data show that CO exposure reduced subsequent loss of striatal dopamine and reduced subsequent loss of midbrain dopamine cells. Furthermore, CO exposure in the AAV-aSyn model reduced levels of aSyn, reduced numbers of aSyn aggregates, and reduced levels of toxic species of aSyn phosphorylated at serine 129. These results support the used of CO for neuroprotection in patients with PD and related disorders.

Thus provided herein are methods for treating a neurodegenerative disease in a subject, the method comprising orally administering a therapeutically effective amount of carbon monoxide to a subject in need thereof. Also provided are oral, e.g., liquid, compositions comprising carbon monoxide for use in a method of treating a neurodegenerative disease in a subject, the method comprising orally administering a therapeutically effective amount of the carbon monoxide composition to a subject in need thereof.

In some embodiments, the neurodegenerative disease is Parkinson's disease, Alzheimer's disease, dementia with Lewy bodies, multiple systems atrophy, progressive supranuclear palsy, corticobasal degeneration, or Pick's disease, frontotemporal dementia due to TDP-43, progranulin, C9ORF72, or Creutzfeldt-Jacob Disease.

In some embodiments, the methods include orally administering a paste, gel, foam, emulsion, Newtonian liquid, or non-Newtonian liquid in which CO is dissolved, e.g., the oral composition is formulated as a paste, gel, foam, emulsion, Newtonian liquid, or non-Newtonian liquid in which CO is dissolved.

In some embodiments, the CO is dissolved in a carrier comprising water and/or oil.

In some embodiments, the methods include administering a therapeutically effective dose of HBI-002 to the subject.

In some embodiments, the methods include providing a dose sufficient to achieve at least 3, 4, 5, 6, 7, 8, 9, or 10%, up to about 12, 13, 14, 15, or 20% Carboxyhemoglobin (COHb)/total hemoglobin.

In some embodiments, the methods include providing a dose sufficient to achieve 3-12% Carboxyhemoglobin (COHb)/total hemoglobin.

In some embodiments, the methods include administering a dose of 0.2 ml/kg to 10 ml/kg body weight.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-C. Quantification of effect of HBI-002 on brain levels of heme oxygenase 1 (HO-1) (P=0.038, N=14), Growth Derived Neurotrophic Factor (GDNF), and LC3B-II.

FIGS. 7A-C. Effect of single dose inhaled CO in the MPTP model. CO (225 ppm; 1 hr) or air (1 hr) administered 1 hr after MPTP or saline injection (normal control saline data not shown; no difference between groups in normal control animals). Animal sacrifice 5 days after MPTP. A. CO preserved striatal dopamine (DA) (P<0.03, t-test; 22 mice/grp). Striatal DA levels measured with HPLC, B. CO reduced loss of substantia nigra pars compacta (SNpc) tyrosine hydroxylase-positive (TH+) neurons. C. Stereological nigral TH+ neuron counts after CO treatment or air (P<0.05, t-test). Mean±std error.

DETAILED DESCRIPTION

Figure 1A:
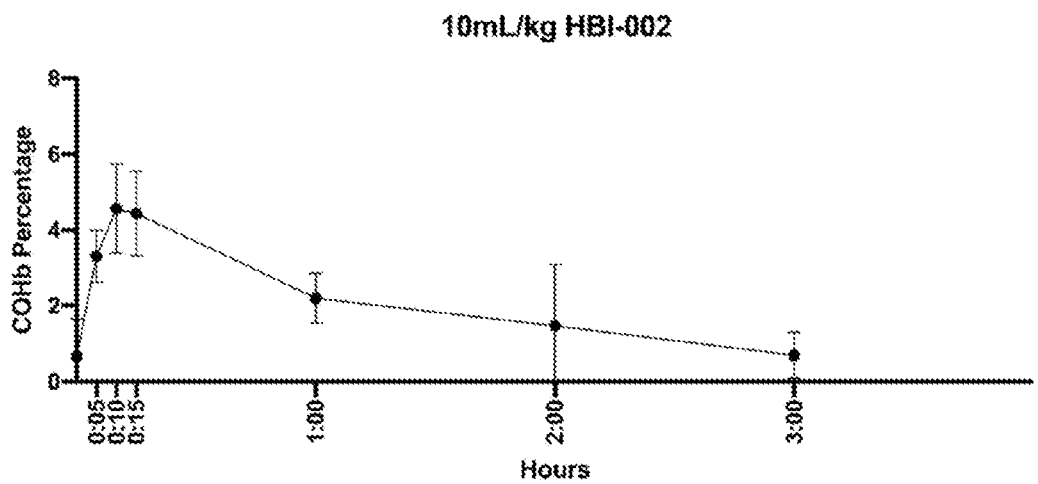
FIG. 1A-C. Blood COHb levels in normal mice after three different doses of oral HBI-002. t=0 values are pre-treatment, n=3 mice for each time point of each dose.
Figure 1B:
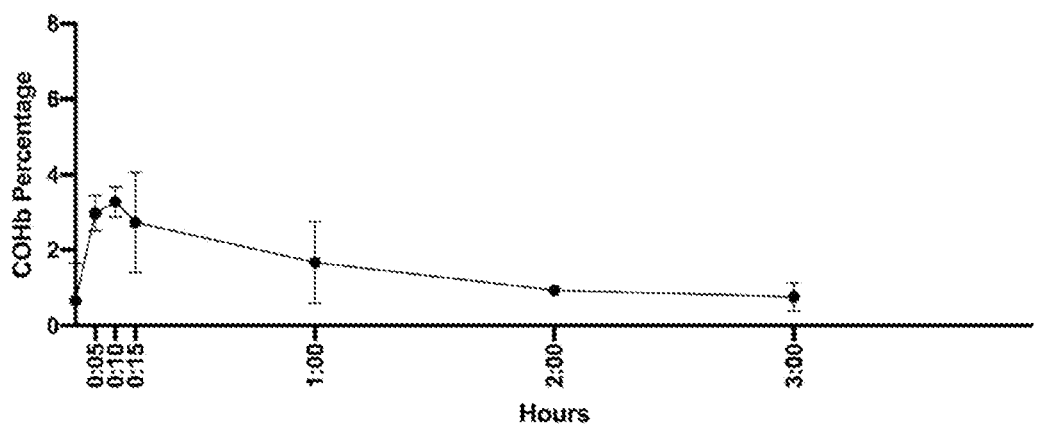
Figure 1C:
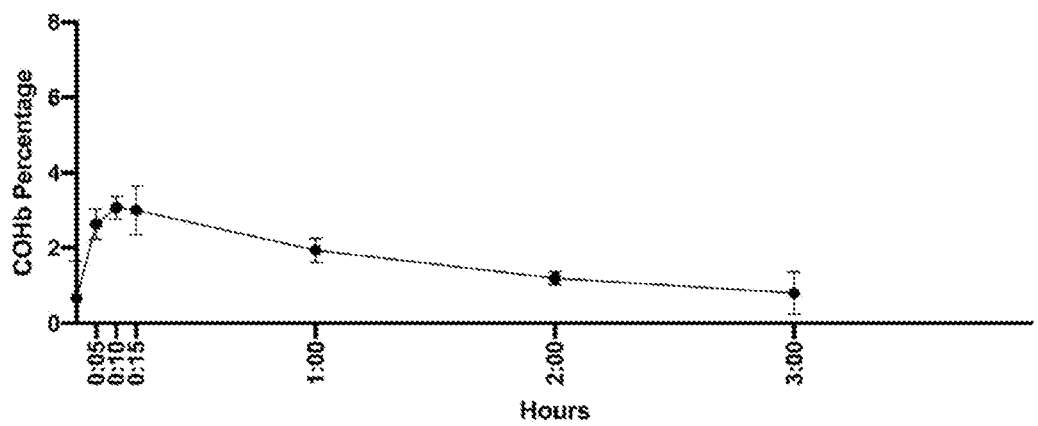

No neuroprotective agents have yet been identified to prevent or slow the course of Parkinson's disease (PD) or Alzheimer's disease, progressive and fatal diseases, and finding such therapeutics is a research imperative.

Despite the known toxicity of CO at high concentration, CO at low concentration is now accepted as capable of regulating a host of physiologic processes[1,2]. Accumulating data have demonstrated that CO, at low concentrations, exerts key physiological functions in various models of tissue inflammation and oxidative injury. Specifically, the literature shows that low dose CO provides potent neuroprotection in PD model[3]. and in models of other neurological disease including including Alzheimer's[4], traumatic brain injury[5], stroke[678-910], and multiple sclerosis[11,12] as well as in in vitro models of apoptosis and oxidative injury[13], 13[14-15],[16]. In each instance, the protection observed was associated with an inhibition in the inflammatory response or a reduction in oxidative stress and cell death. Importantly, low dose CO has been shown to upregulate Nrf2, a transcription factor associated with anti-inflammatory and anti-oxidative properties and implicated in PD[17],[18-23]. Moreover, CO readily crosses the blood-brain barrier, providing facile access to the CNS.

However, the use of inhaled low dose CO is associated with a certain amount of risk as well as adverse feeling in the art due to its association with toxicity. CO at high doses is known to be neurotoxic and potentially fatal, causing irreversible brain damage and parkinsonism in survivors, including damage to critical brain structures such as the globus pallidus and the hippocampus. Indeed, exposure to gaseous CO was previously reported to be associated with an increased risk of dementia (Chang et al., PLoS ONE 9(8): e103078. doi:10.1371/journal.pone.0103078).

Two formulations of CO have been studied to date in the clinic: (1) gaseous CO (iCO) provided by inhalation, and (2) CO bound to CO releasing molecules (CORMs) provided through intravenous injection. 25 phase I and II clinical trials have demonstrated safety of CO administration in the goal dose range of <10% CO-hemoglobin. However, considerations of dosing reliability, patient compliance, and patient and environmental safety complicate the use of CO gas, and toxicity of transition metal carriers, stability issues, and bioavailability issues have been found with CO administration via CORMs. These concerns are heightened with chronic administration, as would likely be needed in PD, AD, and other neurodegenerative diseases. Administration of CO via an oral formulation obviates these concerns, providing a safe and reliable dosing strategy for CO administration.

The present disclosure demonstrates that oral formulations that deliver CO are safe and therapeutically useful in PD and AD.

Methods of Treatment

The methods described herein include methods for the treatment of disorders associated with neurodegeneration. In some embodiments, the disorder is an alpha-synucleinopathy, e.g., PD, dementia with Lewy bodies, or multiple systems atrophy. In other embodiments, the disorder is a combined amyloidopathy and tauopathy, e.g., AD, or a tauopathy, e.g., progressive supranuclear palsy, corticobasal degeneration, or Pick's disease, or another proteinopathy, e.g., frontotemporal dementia due to TDP-43, progranulin, or C9ORF72, or a prionopathy, e.g., Creutzfeldt-Jacob Disease. Generally, the methods include administering a therapeutically effective amount of an oral formulation of CO as described herein, e.g., HBI-002, to a subject who is in need of, or who has been determined to be in need of, such treatment. Thus the present methods can include administration of oral CO, e.g., in a liquid, including Newtonian and non-Newtonian liquids, such as pastes, gels, foams, emulsions, and other non-gaseous compositions, in which CO is dissolved at an amount that, when administered to a subject, provides a therapeutically or prophylactically effective amount of CO to the subject. See, e.g., U.S. Pat. No. 9,980,981. The results presented herein demonstrate efficacy in models of PD and AD.

As used in this context, to "treat" means to ameliorate at least one symptom of the disorder associated with neurodegeneration, or to slow progression of the disorder; the present methods can also be used to reduce a subject's risk of developing the disease (e.g., in subjects who have REM sleep behavioral disorders or a family history or genetic predisposition to develop the disease). Symptoms of Parkinson's disease include: tremors, slowness of voluntary movements, change in gait, and unsteady balance, in addition to nonmotor symptoms including cognitive dysfunction such as memory loss, confusion, loss of ability to plan or complete familiar tasks, withdrawal, hallucinations, and mood changes; thus, administration of a therapeutically effective amount of a compound described herein to a subject with PD can result in a reduction in any of these symptoms, a return or approach to normal motor control and nonmotor function, or the mitigation of further loss of function. Symptoms of cognitive dysfunction associated with Alzheimer's disease include: memory loss, confusion, loss of ability to plan or complete familiar tasks, speech deficits, withdrawal, and mood changes; thus, administration of a therapeutically effective amount of a compound described herein to a subject with AD can result in a reduction in any of these symptoms, a return or approach to normal cognitive function, or the mitigation of further loss of function.

In some embodiments of the methods of treatment described herein, the method can result in increasing the life span of the subject.

In some embodiments of the methods of treatment described herein, the method can result in an improvement in the movement and/or motor function and/or cognitive function of the subject.

Administering may be performed, e.g., at least once (e.g., at least 2-times, at least 3-times, at least 4-times, at least 5-times, at least 6-times, at least 7-times, at least 8-times, at least 9-times, at least 10-times, at least 11-times, at least 12-times, at least 13-times, or at least 14-times) a week. Also contemplated are monthly treatments, e.g. administering at least once per month for at least 1 month (e.g., at least two, three, four, five, or six or more months, e.g., 12 or more months), and yearly treatments (e.g., administration once a year for one or more years).

In some embodiments, an oral formulation of CO is administered daily for subjects with PD and related disorders and for all patients at risk of developing PD and related disorders.

Parkinson's Disease (PD)

Although the neuropathology of PD is well-characterized, including aggregates of alpha-synuclein (aSyn) that accumulate in Lewy bodies in dopamine (DA) neurons of the substantia nigra pars compacta (SN) and other brain cells in association with their progressive degeneration, the etiology of PD is unclear. Oxidative stress, inflammation, and apoptosis all appear to be important contributors[24,25-26,27]. DA cells are particularly vulnerable to oxidative stress, as DA auto-oxidation produces reactive oxygen species that can impair mitochondrial function and induces apoptosis[24,28,29-30,31]. In addition, neuroinflammation appears to be an important contributor to PD pathogenesis[25-27]. PD is a leading cause of death and long-term disability worldwide. In the US, ~500,000 Americans live with PD, with ~50,000 patients diagnosed annually[32]. The annual cost of PD in the US is approximately $25 billion[33].

It is well supported that smoking is linked to a protective effect in PD. However, the strong hypothesis in the scientific community has been that nicotine was the active neuroprotective molecule, in part because of the known neurotoxic effect of CO at high doses. However, two clinical studies with nicotine, the most rigorous of which only recently concluded, showed no protective effect from nicotine in PD patients.

Methods for identifying a subject with PD are known in the art.

Alzheimer's Disease

A cascade of neurodegeneration underlies the relentless, progressive, and irreversible cognitive failure characteristic of Alzheimer's disease (AD). Aβ1-42 aggregates in amyloid plaques, tau protein in neurofibrillary tangles and cell death comprise the classical neuropathological findings[34]. Lewy bodies are frequently observed as well.[35,36,37,38,39] In addition, recent evidence points to key roles for inflammation, mitochondrial dysfunction, Ca2+ dysregulation and aberrant neuronal activity[34,40]. AD is a leading cause of death and disability and the most common form of dementia in the US, with ~5 million people living with AD in the US[41]. The cost of AD to the US healthcare system is substantial, projected at approximately $200 billion in 2010[42]. To date, no neuroprotective agents have yet been identified to slow the course of this devastating and fatal disease, and finding such therapeutics remains a critical unmet need.

HO-1, the enzyme that produces endogenous CO among other catabolites, has been shown to be up-regulated in Alzheimer's disease, leading many in the field to hypothesize that the up-regulation of HO-1, such as occurs with CO, could be neuroprotective in Alzheimer's disease (AD). Moreover, preclinical in vivo studies have been conducted demonstrating that elevation of HO-1 is associated with improved cognitive function[43] and neuroprotection[41,42].

Methods for identifying a subject with AD are known in the art.

HBI-002

HBI-002 is a novel oral drug product containing CO that has been demonstrated to increase CO levels in animals in vivo without apparent safety issues (FIG. 1A). HBI-002 consists of a liquid formulation containing CO and generally recognized as safe (GRAS) substances (see U.S. Pat. No. 9,980,981). HBI-002 permits precise chronic delivery unlike other forms of CO, including iCO or carrier-molecule bound CO (CORMs). Bioavailable CO with oral administration of HBI-002 has been demonstrated in mice (FIG. 1A), documenting that oral HBI-002 administration leads to rapid CO bioavailability in the circulation measured as an increase in COHb saturation, with COHb level increasing in a dose-dependent manner.

The targeted dose of oral HBI-002 to achieve COHb levels of <10% is achievable in rodents (FIG. 1A and Belcher et al.[44]); this is well below the COHb level where toxicity is first observed (~20%[45]; see below), and the targeted dose of oral HBI-002 to achieve COHb levels of 3-7% is achievable in subjects with PD and AD.

EXAMPLES

The invention is further described in the following examples, which do not limit the scope of the invention described in the claims.

Material and Methods

The following materials and methods were used in Example 1 below.

Study Design

AAV-aSyn Experiments

Our objective was to investigate the ability of CO therapy to mitigate the cytotoxic effects of pathogenic aSyn in vivo. Our strategy was to use an established adeno-associated virus (AAV) expression system to overexpress mutant human aSyn in rats which leads to a pathology that closely mimics human PD pathology. Because the substantia nigra has limited connectivity across hemispheres, we performed bilateral stereotactic surgery to deliver viral particles directly into the substantia nigra. One hemisphere received AAV overexpressing aSyn while the other received the same expression system with an empty vector to act as an internal control. Following post-operative recovery, rats were treated with single daily doses of HBI-002 at a dose of 10 mL/kg. Since HBI-002 is given orally via a gavage needle, maximum doses are limited by stomach volume. A dose of 10 mL/kg is nearly a full stomach volume for a rat and therefore was chosen as our maximum once daily dose which leads to similar levels observed in smokers.

After 16 days of treatment with HBI-002, we performed quantitative analysis on the amount of dopamine present in the striatum using HPLC-ECD. We also used stereology to count the number of dopaminergic cells in the substantia nigra using tyrosine hydroxylase (TH) as a marker. Since the overexpression of proteins or the use of xenobiotics could potentially lead to changes in TH expression patterns, we also stained for the general neuronal marker NeuN and performed stereology to control for any potential variation on TH expression.

Since the aggregation and phosphorylation of aSyn are found in PD, we investigated the effect of CO therapy on these endpoints as well. We employed the use a monoclonal antibody specific to human aSyn to assess the extent of aSyn pathology. Similarly, we used an antibody specific to aSyn with a phosphorylated serine 129 residue.

We investigated the mechanism by which CO exerts a neuroprotective effect by first examining the multiple therapeutic targets described in related indications with CO intervention. These potential routes were investigated by assessing changes in protein expression by western blotting or by assaying increased nuclear factor activity with ELISAs.

In all experiments, rats were randomly assigned to treatment groups. Experimenters were blinded to treatment group while performing stereotactic surgery to deliver viral particles and when preforming data collection and analysis. To ensure statistical power, experiments consisted of a minimum of 8 animals. In some cases, experimental endpoints were replicated in independent experiments. Data from these experiments are presented in aggregate in figures. The number of rats used in each experiment, replicated experiments, and the statistical test used are described in the figure legends.

Reagents

HBI-002 was provided by Hillhurst Biopharmaceuticals, Inc. (Montrose, CA). HBI-002 was prepared following the procedure outlined in patent number U.S. Pat. No. 9,980,981. AAV vectors were purchased from Vigene Biosciences (Rockville, MD)

Overexpression of Human A53T aSyn in the SNpc of Rats

Female Sprague Dawley rats ranging from 220-240 g were purchased from Charles River (Wilmington, Mass.) and housed in Center for Comparative Medicine at Massachusetts General Hospital's Institute for Neurodegenerative diseases with a 12 hr light/dark cycle and access to food and water ad libitium. All experiments were approved by Massachusetts General Hospital's institutional animal care and use committee. After one week of acclimation, rats were anesthetized with isoflurane/oxygen and underwent bilateral stereotactic surgery as previously described with minor modifications. Each animal received 2 µL of a $5 \times 10^{12}$ GC/mL viral titer injected into the nigra at the following coordinates: AP: −5.2, ML: +/−2.0, DV: −7.8. The left nigra was given AAV1/2-CMV-empty vector-WPRE-BGH-polyA and the right nigra was given AAV1/2-CMV-human-A53T-alpha-sunuclein-WPRE-BGH-polyA. Animals were allowed to recover for 5 days before therapeutic interventions began.

Low Dose CO Therapy

HBI-002 or vehicle (HBI-002 formulation without CO) was given to animals via oral gavage (14 G needle) at a dose of 10 mL/kg/day. Both HBI-002 and vehicle were stored at 4° C. Freshly opened vials were stored on ice while in use and discarded within 5 minutes after opening to ensure consistent concentrations of CO.

Quantification of Dopamine by HPLC-ECD

Dopamine was quantified as previously described with minor modifications. Rats were deeply anesthetized with ketamine and xylazine (dose) followed by rapid decapitation and brain removal. The striatum from each hemisphere was segregated, dissected on ice, and frozen on dry ice. Pieces of frozen striatum were weighed and homogenized in buffer containing 0.1 mM EDTA, 1 µM 3,4 dihydroxybenzlamine hydrobromide (DHBA, internal standard), and 50 mM phosphoric acid in a 1:20 ratio (weight: volume). The resulting homogenate was centrifuged at 14,000×g to pellet cell debris and precipitated protein. The supernatant was then filtered through Costar SpinX 0.22-micron spin filter cartridges. After filtering, 5 µL of supernatant was injected onto a Microsorb-MV column (C18, 150 mm×5.6 mm, 5 micron) using an Ultimate 3000 UHPLC system (Thermo Fisher). Separation was achieved with a 17-minute isocratic method at a flow rate of 0.6 mL/min, and a mobile phase consisting of 75 mM sodium phosphate monobasic, 1.75 mM sodium-1-octanesulfonate, 100 µL/L triethylamine, 25 µM EDTA, and 10% acetonitrile. Detection was carried out with an Ultimate 3000 ECD-3000RS (Thermo Fisher) with a screening electrode set to −150 mV and a detection electrode set to 250 mV. DHAB was used as a variable internal standard and dopamine was concentration was calculated from a standard curve.

Preparation of Nuclear and Cytosolic Extracts

Unfixed brain tissue from the substantia nigra was collected after 16 days of HBI-002 or vehicle treatment. Nuclear and cytosolic extracts were prepared using a nuclear extraction kit (Abcam, ab113474) following the manufacturer's instructions. After extraction, protein concentration was determined using a NanoDrop microvolume spectrophotometer (Thermo Fisher).

Immunohistochemistry

After 16 days of HBI-002 or vehicle treatment, animals were deeply anesthetized with ketamine and xylazine (dose) followed by rapid decapitation and brain removal. Brains were fixed for 3 days in 4% paraformaldehyde. After that time, brains were sectioned at 40 µm on a vibratome (Leica, Buffalo Grove, Ill.). Sections were collected in a 1 in 6 series and stored in PBS at 4° C.

For each antigen, a single series of sections were stained from each animal. Free-floating sections were incubated in 3% hydrogen peroxide for 15 minutes to block endogenous peroxidase. Next, sections were blocked and permeabilized in PBS with 2.5% bovine serum albumin (BSA), 10% normal goat serum (NGS), and 0.3% Triton X-100 for 30 minutes. Sections were then transferred to wells containing the corresponding primary antibody diluted in PBS with 2.5% BSA and 10% NGS. Sections were allowed to incubate overnight at 4° C. After several washes in PBS, antigens were visualized using an avidin-biotin detection system (ABC elite kit, Vector, Burlingame, Calif.) with ImmPact VIP and DAB substrates (Vector, Burlingame, Calif.) following the manufacturers' instructions. Sections were mounted, dehydrated in graded ethanol, cleared in xylene, and cover slipped with permanent mounting media (Vecta-Mount, Vector, Burlingame, Calif.). Staining intensity was quantified as previously reported.

Immunoblotting

Nuclear and cytosolic protein extracts were diluted in 2× Laemmli sample buffer and heated at 70° C. for 10 minutes. After brief centrifugation, 20 µg of protein was loaded into each lane of 4-20% polyacrylamide gels. Electrophoresis was carried out at 150 V for 1 hour. Then, proteins were transferred to PVDF membranes, washed in distilled water, and dried overnight at 4° C. After reactivation of the PVDF membrane in methanol, total protein per lane was quantified using Revert 700 total protein stain and an Odyssey CLx imaging system (Licor, Lincoln, Nebr.) on the 700 nm channel per the manufacturer's instructions. Membranes were then blocked in 5% dry non-fat milk powder in TBS for 2 hours at room temperature followed by overnight incubation at 4° C. in primary antibody diluted in 5% dry non-fat milk powder in TBS-T. After several washes in TBS-T, membranes were incubated in a 1:30,000 dilution of IRDye 800 donkey anti-rabbit (Licor, Lincoln, NE) in 5% dry non-fat milk powder and 0.02% SDS in TBS-T for 1 hour at room temperature. After several washes in TBS-T followed by a final wash in TBS, blots were imaged with an Odyssey CLx imaging system on the 800 nm channel. Fluorescent intensity of bands was determined using Image Studio (Licor, Lincoln, NE) and bands were normalized to total protein load in individual lanes.

Stereology

Stereology was carried out as previously described with minor modifications. Sections labeled with TH, NeuN, and aSyn underwent counting using the optical fractionator principles with CAST stereology software (Olympus, Tokyo, Japan). Counting was limited to the substantia nigra and was done with a 20× objective with a meander sampling of 100% to count the entire region. A total of eight sections were counted per animal.

Statistical Analysis

All data was analyzed using Prism 8 (GraphPad) with unpaired, two-tailed t-tests. In all experiments, alpha was predetermined to be set at 0.05. Effect sizes and experimental power were calculated using G*Power 3.1 (University of Dusseldorf, Dusseldorf, Germany).

Example 1. HBI-002 is Neuroprotective in PD

This Example explores the neuroprotective potential of CO for PD, providing data in two well established PD models: (i) rat AAV-α-synuclein (aSyn) genetic model and (ii) the mouse MPTP toxin model.

Figure 2A:
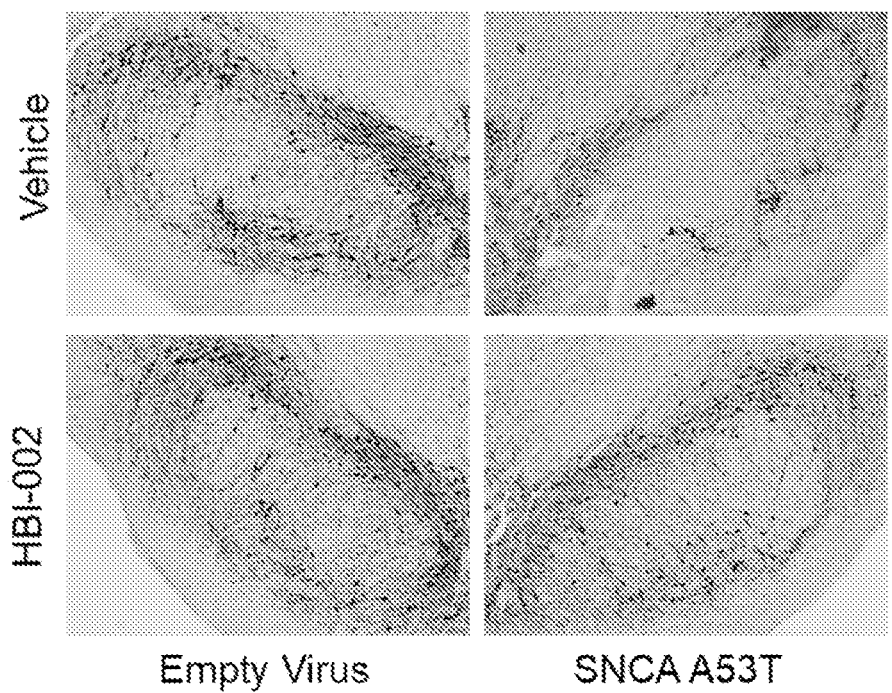
FIGS. 2A-C. Effect of oral HBI-002 in the aSyn model. HBI-002 (10 ml/kg) or vehicle (10 ml/kg) dosed daily for 3 wks following injection of AAV-aSyn or AAV with no transgene. Animal sacrifice 3 wks after AAV. A. HBI-002 reduced loss of substantia nigra pars compacta (SNpc) tyrosine hydroxylase-positive (TH+) neurons. B. Compared to treatment with vehicle, treatment with HBI-002 preserved striatal DA (p=0.026, t-test; 10 vehicle and 8 HBI-002 rats/grp), C. Stereological TH+ neuron counts in the SNpc are preserved after HBI-002 treatment compared to Vehicle (p<0.01, t-test). Analyses blind to treatment. Mean±std error.
Figure 2B:
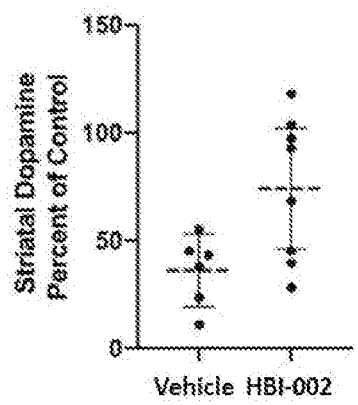
Figure 2C:
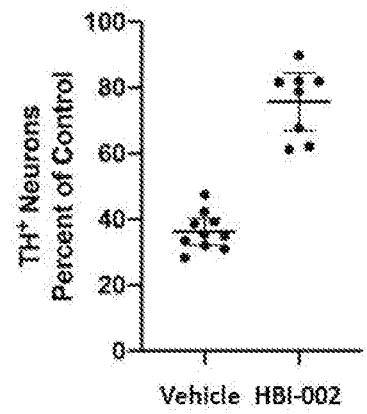
Figure 3A:
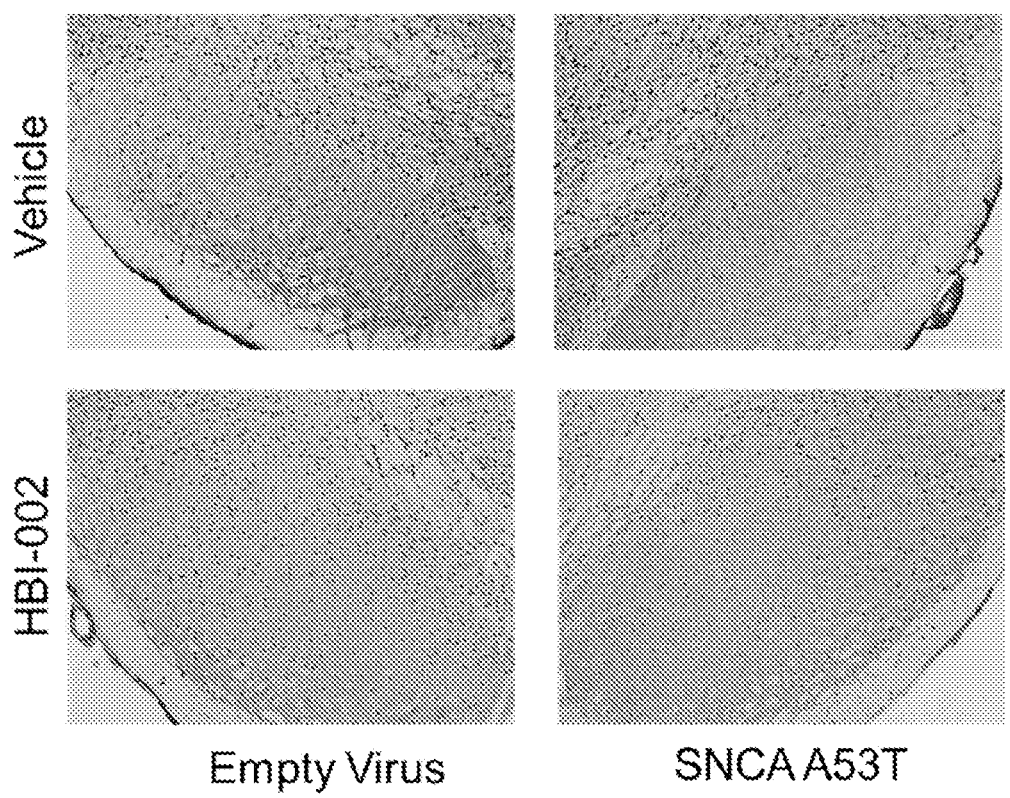
FIGS. 3A-B. Representative stereological photomicrographs and quantification of effect of HBI-002 treatment on NeuN+ cells in the substantia nigra. *** P=0.001, N=15
Figure 3B:
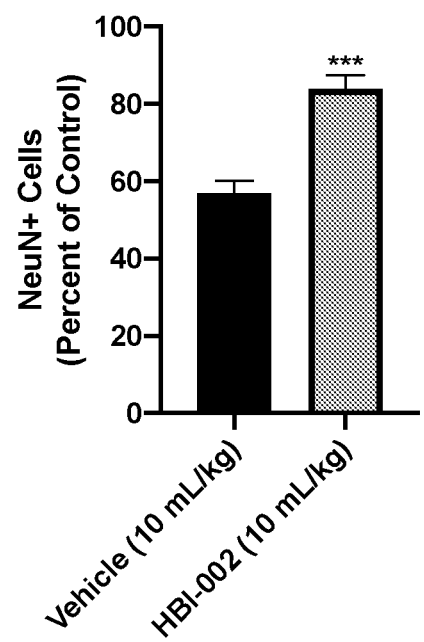

In the AAV-aSyn rat model, AAV is used to deliver human aSyn harboring the A53T mutation directly into the SNpc, leading to cell loss over 3 weeks in association with aSyn oligomerization[46,47] (FIG. 2A).[48,49,50]. After AAV-aSyn was injected into the right SNpc and AAV containing no aSyn transgene was injected into the left SNpc, rats were treated with either HBI-002 (10 mL/kg; n=8) or vehicle (10 mL/kg; n=10) via oral gavage, daily for 3 wks. Striata and midbrains were harvested, and we measured DA levels in the left and right striata via HPLC, blinded to treatment. Rats treated with vehicle showed preservation of only 36.05%±6.56% of right striatal DA compared to the left side. In contrast, rats treated with HBI-002 retained 74.09%±11.85% of right striatal DA compared to left (p=0.026, t-test) (FIG. 2B). We next used standard stereological methods to count tyrosine hydroxylase (TH)-positive neurons in the SNpc, blinded to treatment. Critically, while vehicle was associated with reduction of right SNpc TH+ neurons to 36.2%±1.82% compared to the left side, HBI-002 treatment was associated with increased preservation of right-sided TH+ cell counts to 75.7%±3.73% compared to the left (p=0.0001, t-test) (FIG. 2C). The same treatment also reduced loss of nigral cells (p=0.0001, t-test) (FIGS. 3A-B).

Figure 4A:
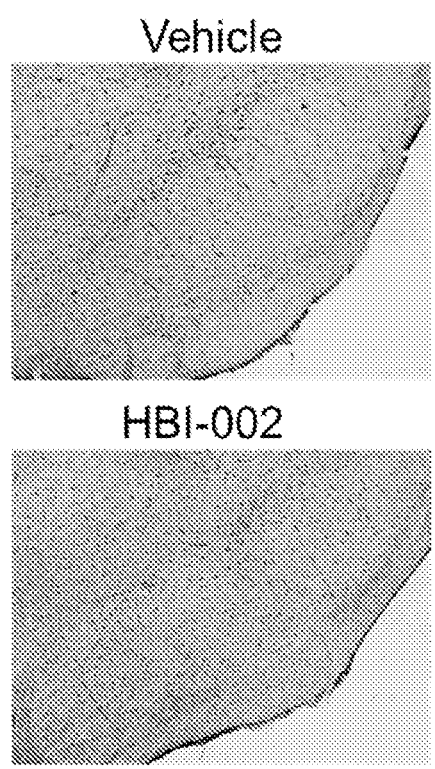
FIGS. 4A-B. Representative stereological photomicrographs and quantification of effect of HBI-002 treatment on aggregated aSyn in the substantia nigra. * P=0.0166, N=8
Figure 4B:
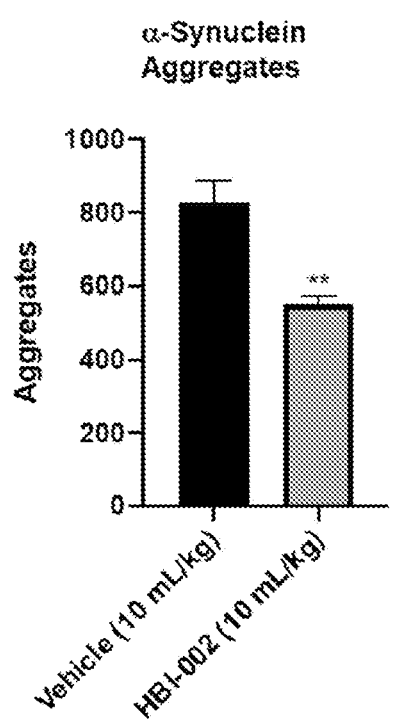
Figure 5A:
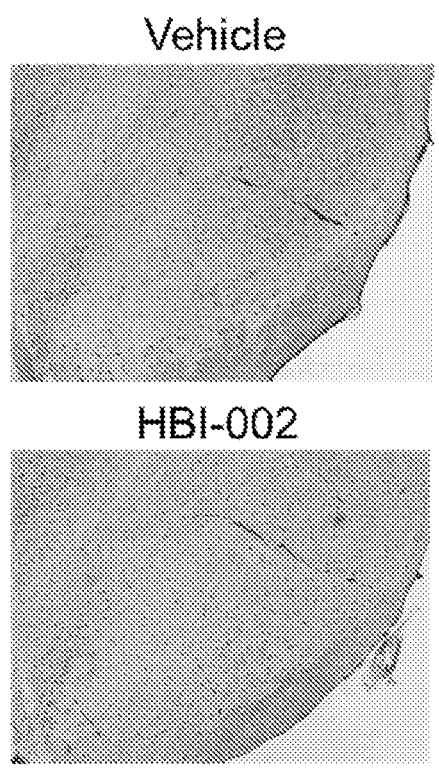
FIGS. 5A-B. Representative stereological photomicrographs and quantification of effect of HBI-002 treatment on phosphorylated serine 129 aSyn in the substantia nigra. ** P=0.0053, N=8.
Figure 5B:
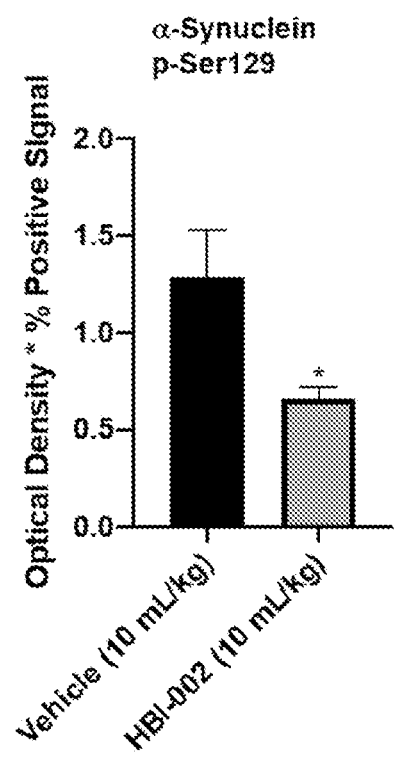

In addition, treatment with HBI-002 reduced synuclein aggregates (p=0.0166, t-test) (FIG. 4A-B). HBI-002 treatment also reduced levels of synuclein phosphorylated on Ser129 (p=0.0053, t-test) (FIGS. 5A-B), a pathological feature of PD that potentially contributes to aSyn A53T toxicity[51].

Figures 6A, 6B:
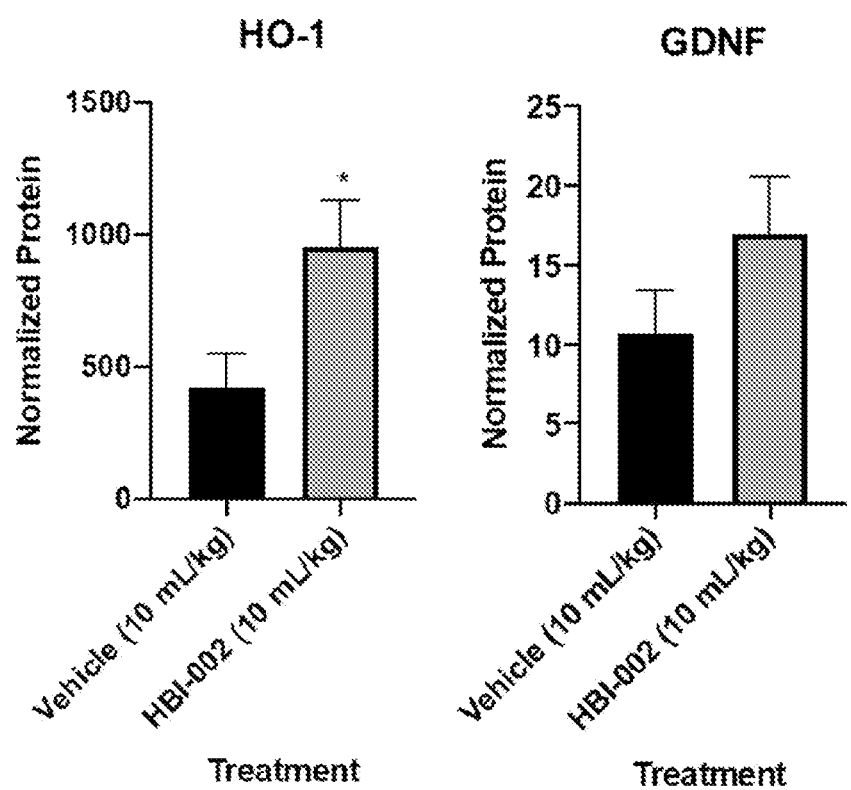

Biochemical analysis showed engagement of HO-1 (p=0.038, t-test), GDNF, and LC3B-II (FIGS. 6A-C).

These results indicate that oral CO is neuroprotective in an animal model of PD.

Figure 7C:
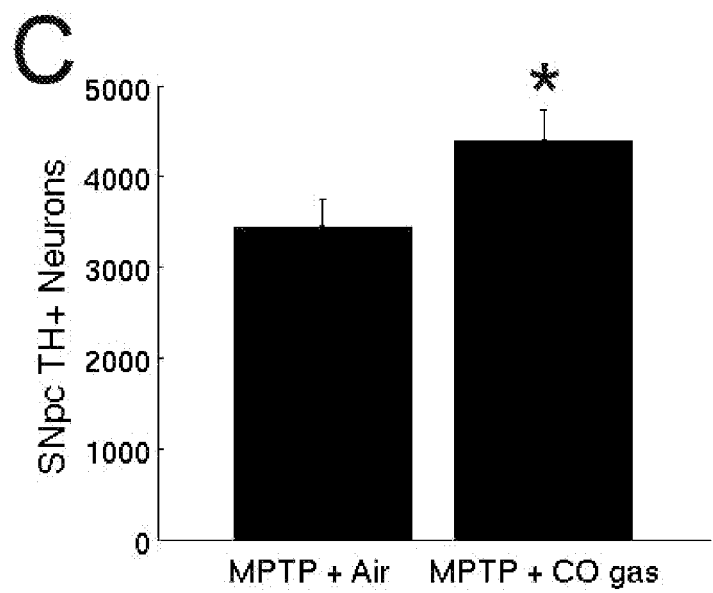

We also employed a short-term regimen of the widely used[52,53] MPTP toxin model in which DA loss ensues within 5-8 days of MPTP. We elected to initiate iCO treatment only after MPTP exposure in order to model protective treatment of human PD, which begins only after disease onset. We exposed mice to MPTP (40 mg/kg, i.p.)[54,55] or saline (study control) and then treated with a single dose of either iCO (225 ppm) or air (negative control) for 1 hr, for 4 total groups: 1) MPTP/CO (225 ppm; 1 hr), 2) MPTP/air (1 hr), 3) saline/CO (225 ppm; 1 hr), 4) saline/air (1 hr). Five days after MPTP exposure, we measured DA levels in the striata via HPLC and counted TH+ neurons in all groups. MPTP mice treated with CO had ~46% higher DA levels than those treated with air (2-tailed t-test, p=0.028; FIG. 7A). CO did not alter DA levels in saline-treated mice (air: 96.7±1.9 pmol/mg, iCO: 97.0±2.4 pmol/mg, p>0.05, n=22 per group). Critically, for TH+ neurons, MPTP mice treated with iCO had ~22% more TH+ neurons than those treated with air (p<0.05; FIGS. 7B-C). In contrast, TH+ cell counts in saline-treated mice were not significantly different: air 7,536±541; iCO 7,437±545, p>0.05. These results in both a genetic model of PD and a toxin model of PD strongly support therapeutic efficacy of HBI-002 for PD.

Example 2. HBI-002 is Neuroprotective in AD

Endogenous CO is generated in the body and brain by the heme oxygenases (HO). These enzymes degrade heme, a toxic species present in several mitochondrial proteins and hemoglobin, into CO, the antioxidant biliverdin, and $Fe^{2+}$[56]. HO-1 is expressed in most cells of the body and brain[57], and both neuronal and non-neuronal CNS cells, including astrocytes and microglia, rapidly upregulate HO-1 in response to stress[58]. HO-1 expression is significantly elevated in the AD brain, with 9-fold elevation in the hippocampus relative to normal controls[59]. Furthermore, in AD, HO-1 colocalizes with tau pathology, including the neurites of senile amyloid plaques, neurofibrillary tangles, and neuropil threads[60]. Potentially due to the divergent properties of HO-1's enzymatic products, including the neuroprotective effects of CO outlined above, the anti-oxidant properties of biliverdin (which is modified to the anti-oxidant bilirubin), and the potential pro-oxidant effects of iron ($Fe^{2+}$), which can deposit in the brain and has been linked to the progression of AD[61], conflicting reports exist about the properties of HO-1 in AD, although several studies have found HO-1 to be protective in AD models[62,63].

To determine whether oral formulation CO (HBI-002) can upregulate HO-1 to engage HO-1 cascades in an animal model of AD beta-amyloidopathy, we studied the effects of HBI-002 in 10-11 month old mice harboring mutations in the amyloid precursor protein (APP) and the presenilin (PSEN) protein (APPswe/PSEN1dE9), known as APP/PS1 mice[64,65]). This AD mouse model forms robust amyloid plaques by 6 months.

APP/PS1 mice were treated with HBI-002 or Vehicle at a dose of 10 mL/kg, once daily, for 14 days. Mice ranged from 10-11 months in age. HO-1 levels in the hippocampus were determined with Western blot.

Figure 8A:
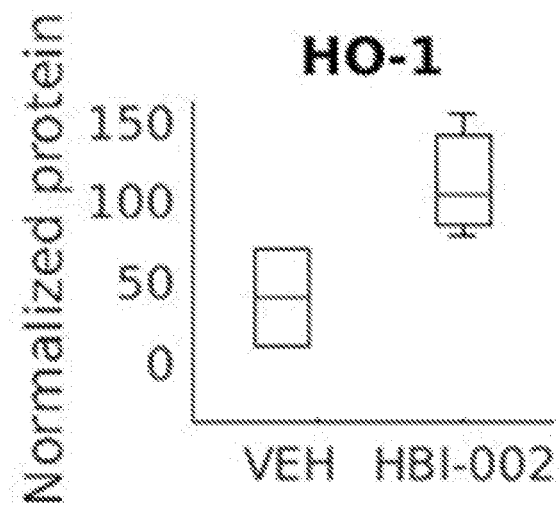
FIGS. 8A-B. HBI-002 treatment increased expression of HO-1 in hippocampus in the APP/PS1 mouse model of AD (A) and wild type mice (B).
Figure 8B:
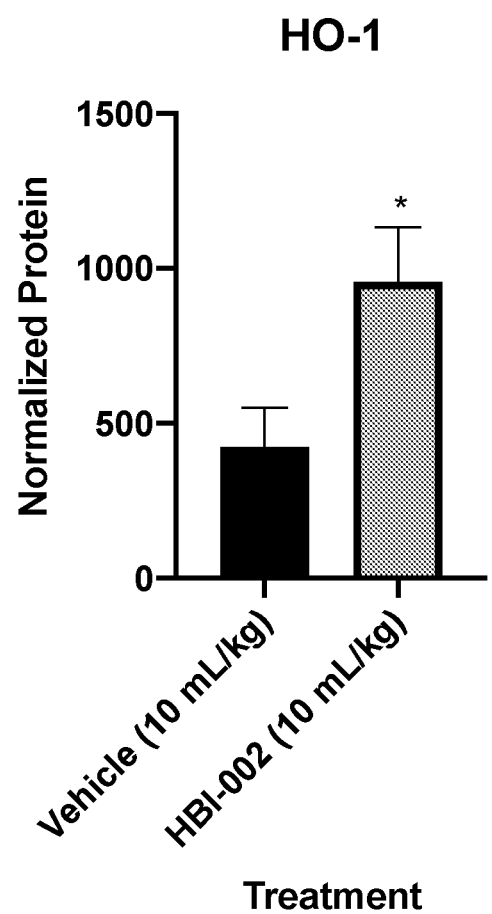

In APP/PS1mice, CO treatment via oral gavage was associated with increased HO-1 expression in the hippocampus (FIG. 8A). These results are consistent with findings in wild-type (WT) mice, where oral HBI-002 treatment also increased HO-1 expression (p=0.038, t-test; n=14 per group (FIG. 8B)).

These results show that oral CO formulation (HBI-002) increases HO-1 expression in the APP/PS1 model of AD. Together with prior results demonstrating that CO is neuroprotective in AD models[66] and prior results linking HO-1 associated molecular cascades to neuroprotection in AD[41,42] and to improved cognitive function[26] these findings support therapeutic efficacy of an oral formulation CO in AD.

REFERENCES

1. Motterlini R, Otterbein L E. The therapeutic potential of carbon monoxide. Nat Rev Drug Discov. 2010; 9:728-43.
2. Prabhakar, N. R., Dinerman, J. L., Agani, F. H., Snyder, S. H. 1995. Carbon monoxide: A role in carotid body chemoreception. PNAS. 92:1994-1997.
3. Moon, H., Jang, J. H., Jang, T. C., & Park, G. H. Carbon Monoxide Ameliorates 6-Hydroxydopamine-Induced Cell Death in C6 Glioma Cells. Biomolecules & Therapeutics. 2018; 26(2), 175-5.
4. Hettiarachchi N, Dallas M, Al-Owais M, Griffiths H, Hooper N, Scragg J, Boyle J, Peers C. Heme oxygenase-1 protects against Alzheimer's amyloid-β(1-42)-induced toxicity via carbon monoxide production. Cell Death Dis. 2014 Dec. 11; 5:e1569.
5. Choi Y K, Maki T, Mandeville E T, Koh S H, Hayakawa K, Arai K, Kim Y M, Whalen M J, Xing C, Wang X, Kim K W, Lo E H. Dual effects of carbon monoxide on pericytes and neurogenesis in traumatic brain injury. Nat Med. 2016 November; 22(11):1335-1341.
6. Wang B, Cao W, Biswal S, Doré S. Carbon monoxide-activated Nrf2 pathway leads to protection against permanent focal cerebral ischemia. Stroke. 2011 September; 42(9):2605-10.

7. Klaus J A, Kibler K K, Abuchowski A, Koehler R C. Early treatment of transient focal cerebral ischemia with bovine PEGylated carboxy hemoglobin transfusion. Artificial cells, blood substitutes, and immobilization biotechnology 2010; 38:223-9.
8. Zhang J, Cao S, Kwansa H, Crafa D, Kibler K K, Koehler R C. Transfusion of hemoglobin-based oxygen carriers in the carboxy state is beneficial during transient focal cerebral ischemia. Journal of Applied Physiology 2012; 113:1709-17.
9. Zeynalov E, Doré S. Low Doses of Carbon Monoxide Protect Against Experimental Focal Brain Ischemia. Neurotoxicity research. 2009; 15(2):133-137.
10. Schallner N, Pandit R, LeBlanc R, 3rd, et al. Microglia regulate blood clearance in subarachnoid hemorrhage by heme oxygenase-1. The Journal of Clinical Investigation 2015; 125:2609-25.
11. Chora A A, Fontoura P, Cunha A, et al. Heme oxygenase-1 and carbon monoxide suppress autoimmune neuroinflammation. The Journal of Clinical Investigation 2007; 117: 438-47.
12. Fagone P, Mangano K, Coco M, et al. Therapeutic potential of carbon monoxide in multiple sclerosis. Clinical and Experimental Immunology 2012; 167: 179-87.
13. Vieira H L, Queiroga C S, Alves P M. Preconditioning induced by carbon monoxide provides neuronal protection against apoptosis. J Neurochem 2008; 107: 375-384
14. Queiroga C S, Vercelli A, Vieira H L. Carbon monoxide and the CNS: challenges and achievements. British journal of pharmacology 2014. Br J Pharmacol. 2015 March; 172(6):1533-45.
15. Almeida A S, Queiroga C S, Sousa M F, Alves P M, Vieira H L. Carbon monoxide modulates apoptosis by reinforcing oxidative metabolism in astrocytes: role of Bcl-2. The Journal of Biol Chem 2012; 287:10761-70.
16. Dallas M et al. Carbon monoxide protects against oxidant-induced apoptosis via inhibition of Kv2.1. FASEB. 2011; 25:1519-30.
17. Otterbein L E, et al. Carbon monoxide has anti-inflammatory effects involving the mitogen-activated protein kinase pathway. Nat Med. 2000; 6:422-8.
18. Belcher J D, Young M, Chen C, Nguyen J, Burhop K, Tran P, Vercellotti G M. MP4CO, a pegylated hemoglobin saturated with carbon monoxide, is a modulator of HO-1, inflammation and vaso-occlusion in transgenic sickle cell mice. Blood 2013; 122: 2757-2764.
19. Chi P L, Lin C C, Chen Y W, Hsiao L D, Yang C M. CO Induces Nrf2-Dependent Heme Oxygenase-1 Transcription by Cooperating with Sp1 and c-Jun in Rat Brain Astrocytes. Mol Neurobiol. 2014 Aug. 23.
20. Shin D Y, Chung J, Joe Y, Pae H O, Chang K C, Cho G J, Ryter S W, Chung H T. Pretreatment with CO-releasing molecules suppresses hepcidin expression during inflammation and endoplasmic reticulum stress through inhibition of the STAT3 and CREBH pathways. Blood. 2012 Mar. 15; 119(11): 2523-2532.
21. Chung J, Shin D Y, Zheng M, Joe Y, Pae H O, Ryter S W, Chung H T. Carbon monoxide, a reaction product of heme oxygenase-1, suppresses the expression of C-reactive protein by endoplasmic reticulum stress through modulation of the unfolded protein response. Mol Immunol 2011 September; 48(15-16): 1793-1799.
22. Sawle P, Foresti R, Mann B E, Johnson T R, Green C J, Motterlini R. Carbon monoxide-releasing molecules (CO-RMs) attenuate the inflammatory response elicited by lipopolysaccharide in RAW264.7 murine macrophages. Br J Pharmacol. 2005 July; 145(6): 800-810.
23. Zhang X, Shan P, Alam J, Fu X Y, Lee P J. Carbon monoxide differentially modulates STAT1 and STAT3 and inhibits apoptosis via a phosphatidylinositol 3-kinase/Akt and p38 kinase-dependent STAT3 pathway during anoxia-reoxygenation injury. J Biol Chem. 2005 Mar. 11; 280(10): 8714-8721.
24. Lee Mosley R., Benner E. J., Kadiu I., et al. Neuroinflammation, oxidative stress, and the pathogenesis of Parkinson's disease. Clinical Neuroscience Research. 2006; 6(5):261-281.
25. Hirsch E C, Vyas S, Hunot S. Neuroinflammation in Parkinson's disease. Parkinsonism Relat Disord. 2012; 18 (Suppl 1): S210-2.
26. Hirsch E. C., Hunot S. Neuroinflammation in Parkinson's disease: a target for neuroprotection? The Lancet Neurology. 2009; 8(4):382-397.
27. Hunot S., Hirsch E. C. (2003). Neuroinflammatory processes in Parkinson's disease. Ann. Neurol. 53(Suppl. 3), S49-S58; discussion S58-S60. 10.1002/ana.10481
28. Olanow C W (1990) Oxidation reactions in Parkinson's disease. Neurology 40 (10 Suppl 3):32-37, discussion 37-39.
29. Valente E M, Abou-Sleiman P M, Caputo V, Muqit M M, Harvey K, Gispert S, Ali Z, Del Turco D, Bentivoglio A R, Healy D G, et al. (2004) Hereditary early-onset Parkinson's disease caused by mutations in PINK1. Science 304:1158-1160.
30. Moskowitz M A, Lo E H. Neurogenesis and apoptotic cell death. Stroke. 2003; 34(2):324-326.
31. Naoi M, Maruyama W. Cell death of dopamine neurons in aging and Parkinson's disease. Mech Aging Dev. 1999; 111:175-188.
32. National Institute of Neurological Disorders and Stroke (NINDS). Mar. 23, 2017. Parkinson's Disease Fact Sheet. Retrieved from report.nih.gov/NIHfactsheets/ViewFactSheet.aspx?csid=109
33. The Parkinson's Disease Foundation. Mar. 23, 2017. Statistics on Parkinson's. Retrieved from www.pdf.org/en/parkinson_statistics.
34. Musiek E S, Holtzman D M. Three dimensions of the amyloid hypothesis: time, space and 'wingmen'. Nat Neurosci. 2015 June; 18(6):800-6.
35. Hamilton R L (2000) Lewy bodies in Alzheimer's disease: A neuropathological review of 145 cases using alpha-synuclein immunohistochemistry. Brain Pathol 10, 378-384.
36. Parkkinen L, Soininen H, Alafuzoff I (2003) Regional distribution of alpha-synuclein pathology in unimpaired aging and Alzheimer disease. J Neuropathol Exp Neurol 62, 363-367.
37. Uchikado H, Lin W-L, DeLucia M W, Dickson D W (2006) Alzheimer disease with amygdala Lewy bodies: A distinct form of alpha-synucleinopathy. J Neuropathol Exp Neurol 65, 685-697.
38. Murray M E, Graff-Radford N R, Ross O A, Petersen R C, Duara R, Dickson D W (2011) Neuropathologically defined subtypes of Alzheimer's disease with distinct clinical characteristics: A retrospective study. Lancet Neurol 10, 785-796.
39. Popescu A, Lippa C F, Lee V M Y, Trojanowski J Q (2004) Lewy bodies in the amygdala: Increase of alpha-synuclein aggregates in neurodegenerative diseases with tau-based inclusions. Arch Neurol 61, 1915-1919.

40. Huang Y, Mucke L. Alzheimer mechanisms and therapeutic strategies. Cell. 2012 Mar. 16; 148(6):1204-22.
41. Hebert L E, Weuve J, Scherr P A, Evans D L. Alzheimer disease in the United States (2010-2050) estimated using the 2010 census. Neurology. 2013; 80:1778-83.
42. Hurd M D, Martorell P, Delavande A, Mullen K J, Langa K M. Monetary costs of dementia in the United States. NEJM. 2013; 368(14):1326-34.
43. Opii W O, Joshi G, Head E, Milgram N W, Muggenburg B A, Klein J B, Pierce W M, Cotman C W, Butterfield D A. Proteomic identification of brain proteins in the canine model of human aging following a long-term treatment with antioxidants and a program of behavioral enrichment: relevance to Alzheimer's disease. Neurobiol Aging. 2008 January; 29(1):51-70.
44. Belcher J D, Gomperts E, Nguyen J, Chen C, Abdulla F, Kiser Z M, Gallo D, Levy H, Otterbein L E, Vercellotti G M. Oral carbon monoxide therapy in murine sickle cell disease: Beneficial effects on vaso-occlusion, inflammation and anemia. PLoS One. 2018 Oct. 11; 13(10):e0205194
45. Stewart R D, Peterson J E, Baretta E D, Bachand R T, Hosko M J, Herrmann A. Experimental human exposure to carbon monoxide. Arch Environ Health 1970; 21:154-164.
46. McFarland N R, Fan Z, Xu K, Schwarzschild M A, Feany M B, Hyman B T, McLean P J. Alpha-synuclein S129 phosphorylation mutants do not alter nigrostriatal toxicity in a rat model of Parkinson disease. J Neuropathol Exp Neurol. 2009 May; 68(5):515-24.
47. Koprich, J. B., Johnston, H. T., Reyes, M. G., Sun, X., Brotchie, J. M. Expression of human A53T alpha-synuclein in the rat substantia nigra using a novel AAV1/2 vector produces a rapidly evolving pathology with protein aggregation, dystrophic neurite architecture and nigrostriatal degeneration with potential to model the pathology of Parkinson's disease. Molecular Degeneration. 5:43 (2010).
48. Theodore S, et al. Targeted Overexpression of Human α-Synuclein Triggers Microglial Activation and an Adaptive Immune Response in a Mouse Model of Parkinson Disease. J Neuropathol Exp Neurol. 2008; 67:1149-58.
49. Harms A S, et al. MHCII is required for a-synuclein-induced activation of microglia, CD4 T cell proliferation, and dopaminergic neurodegeneration. J Neurosci. 2013 Jun. 5; 33(23):9592-600.
50. Cai W, et al. Bimolecular Fluorescence Complementation of Alpha-synuclein Demonstrates its Oligomerization with Dopaminergic Phenotype in Mice. EBioMedicine. 2018 March; 29:13-22.
51. Sato, H. Neurobiol. Dis. 31, 16884-16894 (2011)
52. Blesa J., et al. Classic and new animal models of Parkinson's disease. 2012. J. Biomed. Biotechnol. 2012:845618.
53. Blandini F, et al. Animal models of Parkinson's disease. FEBS J. 2012 April; 279(7):1156-66.
54. Jackson-Lewis V, Przedborski S. Protocol for the MPTP mouse model of Parkinson's disease. Nat Protoc. 2007; 2(1):141-51.
55. Chen X, Wales P, Quinti L, Zuo F, Moniot S, Herisson F, Rauf N A, Wang H, Silverman R B, Ayata C, Maxwell M M, Steegborn C, Schwarzschild M A, Outeiro T F, Kazantsev A G. The sirtuin-2 inhibitor AK7 is neuroprotective in models of Parkinson's disease but not amyotrophic lateral sclerosis and cerebral ischemia. PLoS One. 2015 Jan. 21; 10(1):e0116919.
56. Kumar S and Bandyopadhyay U. Free heme toxicity and its detoxification systems in human; Toxicol. Lett, 2005; 157 (3), 175-188.
57. Sutherland B A, Rahman R M, Clarkson A N, Shaw O M, Nair S M, Appleton I. Cerebral heme oxygenase 1 and 2 spatial distribution is modulated following injury from hypoxia-ischemia middle cerebral artery occlusion in rats. Neurosci Res. 2009; 65(4):326-334.
58. Dwyer B E, Nishimura R N, Lu S Y. Differential expression of heme oxygenase-1 in cultured cortical neurons and astrocytes determined by the aid of a new heme oxygenase antibody. Response to oxidative stress. Brain Res Mol Brain Res 1995; 30: 37-47.
59. Schipper HM1, Cissé S, Stopa E G. Expression of heme oxygenase-1 in the senescent and Alzheimer-diseased brain. Ann Neurol. 1995 June; 37(6):758-68.
60. Smith M A, Kutty R K, Richey P L, Yan S D, Stern D, Chader G J, Wiggert B, Petersen R B, Perry G. Heme oxygenase-1 is associated with the neurofibrillary pathology of Alzheimer's disease. Am J Pathol. 1994 July; 145(1):42-7.
61. Hettiarachchi N, Dallas M, Al-Owais M, Griffiths H, Hooper N, Scragg J, Boyle J, Peers C. Heme oxygenase-1 protects against Alzheimer's amyloid-β(1-42)-induced toxicity via carbon monoxide production. Cell Death Dis. 2014 Dec. 11; 5:e1569.
62. Wang Y, Miao Y, Mir A Z, Cheng L, Wang L, Zhao L, Cui Q, Zhao W, Wang H. Inhibition of beta-amyloid-induced neurotoxicity by pinocembrin through Nrf2/HO-1 pathway in SH-SY5Y cells. J Neurol Sci. 2016 Sep. 15; 368:223-30
63. Imuta N1, Hori O, Kitao Y, Tabata Y, Yoshimoto T, Matsuyama T, Ogawa S. Hypoxia-mediated induction of heme oxygenase type I and carbon monoxide release from astrocytes protects nearby cerebral neurons from hypoxia-mediated apoptosis. Antioxid Redox Signal. 2007 May; 9(5):543-52.
64. Jankowsky J L, Slunt H H, Ratovitski T, Jenkins N A, Copeland N G, Borchelt D R. Co-expression of multiple transgenes in mouse CNS: a comparison of strategies. Biomol Eng. 2001 June; 17(6):157-65.
65. Jankowsky J L, Fadale D J, Anderson J, Xu G M, Gonzales V, Jenkins N A, Copeland N G, Lee M K, Younkin L H, Wagner S L, Younkin S G, Borchelt D R. Mutant presenilins specifically elevate the levels of the 42 residue beta-amyloid peptide in vivo: evidence for augmentation of a 42-specific gamma secretase. Hum Mol Genet. 2004 Jan. 15; 13(2):159-70.
66. Hettiarachchi N, Dallas M, Al-Owais M, Griffiths H, Hooper N, Scragg J, Boyle J, Peers C. Heme oxygenase-1 protects against Alzheimer's amyloid-β(1-42)-induced toxicity via carbon monoxide production. Cell Death Dis. 2014 Dec. 11; 5:e1569.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a neurodegenerative disease in a subject, the method comprising orally administering a therapeutically effective amount of carbon monoxide (CO) to a subject in need thereof, wherein the therapeutically effective amount comprises a dose sufficient to achieve at least 3% and up to about 20% Carboxyhemoglobin (COHb)/total hemoglobin.

2. The method of claim 1, wherein the neurodegenerative disease is Parkinson's disease, Alzheimer's disease, dementia with Lewy bodies, multiple systems atrophy, progressive supranuclear palsy, corticobasal degeneration, or Pick's disease, frontotemporal dementia due to TDP-43, progranulin, C9ORF72, or Creutzfeldt-Jacob Disease.

3. The method of claim 1, comprising orally administering a paste, gel, foam, emulsion, Newtonian liquid, or non-Newtonian liquid in which CO is dissolved.

4. The method of claim 3, wherein the CO is dissolved in a carrier comprising water and/or oil.

5. The method of claim 1, comprising administering a therapeutically effective dose of HBI-002 to the subject.

6. The method of claim 5, comprising administering a dose of 0.2 ml/kg to 10 ml/kg body weight.

7. The method of claim 1, comprising providing a dose sufficient to achieve at least 4, 5, 6, 7, 8, 9, or 10%, up to about 12, 13, 14, 15, or 20% Carboxyhemoglobin (COHb)/total hemoglobin.

8. The method of claim 7, comprising providing a dose sufficient to achieve 3-12% Carboxyhemoglobin (COHb)/total hemoglobin.

* * * * *